(12) United States Patent
Gajda et al.

(10) Patent No.: US 10,737,237 B2
(45) Date of Patent: Aug. 11, 2020

(54) COMPOSITION AND PROCESS FOR REMOVING CHLORIDES FROM A GASEOUS STREAM

(71) Applicant: UOP LLC, Des Plaines, IL (US)

(72) Inventors: Gregory Gajda, Mount Prospect, IL (US); Mark G. Riley, Hinsdale, IL (US); Charanjeet Singh, Baton Rouge, LA (US)

(73) Assignee: UOP LLC, Des Plaines, IL (US)

( * ) Notice: Subject to any disclaimer, the term of this patent is extended or adjusted under 35 U.S.C. 154(b) by 216 days.

(21) Appl. No.: 15/887,727

(22) Filed: Feb. 2, 2018

(65) Prior Publication Data

US 2018/0154331 A1 Jun. 7, 2018

Related U.S. Application Data

(63) Continuation of application No. PCT/US2016/046270, filed on Aug. 10, 2016.

(Continued)

(51) Int. Cl.
*B01D 46/00* (2006.01)
*B01J 20/08* (2006.01)
(Continued)

(52) U.S. Cl.
CPC .............. *B01J 20/08* (2013.01); *B01D 53/02* (2013.01); *B01D 53/04* (2013.01); *B01D 53/685* (2013.01);
(Continued)

(58) Field of Classification Search
CPC .................. B01J 20/08; B01J 20/28057; B01J 20/28071; B01J 20/0277; B01J 20/3078;
(Continued)

(56) References Cited

U.S. PATENT DOCUMENTS 3,506,732 A * 4/1970 Crowley .................. C07C 7/12
585/831
3,557,025 A 1/1971 Emerson et al.
(Continued)

FOREIGN PATENT DOCUMENTS

CN 1147979 A 4/1997
CN 101505855 A 8/2009
(Continued)

OTHER PUBLICATIONS

M.C. Hales, et al, Thermal Analysis of Smithsonite and Hydrozincite, Journal of Thermal Analysis and Calorimetry, vol. 91 (2008) 3, 855-860.
(Continued)

*Primary Examiner* — Dung H Bui

(57) ABSTRACT

A composition capable of removing chlorides from a gaseous stream and a process of using same. The compositions have sufficient chloride capacity, offer comparable creation of green oil, and have sufficient structural integrity to be utilized as sorbents in a chloride removal process. Generally, the compositions include a first zinc carbonate, a second zinc carbonate different than the first zinc carbonate and an alumina material. The composition has been cured at a temperature between about 149 to 399° C. The first zinc carbonate may comprise hydrozincite and the second zinc carbonate may comprise smithsonite.

19 Claims, 2 Drawing Sheets

Related U.S. Application Data

(60) Provisional application No. 62/204,108, filed on Aug. 12, 2015.

(51) Int. Cl.

| | | |
|---|---|---|
| *B01J 20/06* | (2006.01) | |
| *B01J 20/02* | (2006.01) | |
| *C01G 9/00* | (2006.01) | |
| *B01D 53/02* | (2006.01) | |
| *B01D 53/68* | (2006.01) | |
| *B01J 20/28* | (2006.01) | |
| *C01G 9/04* | (2006.01) | |
| *B01D 53/04* | (2006.01) | |
| *B01J 20/04* | (2006.01) | |
| *B01J 20/30* | (2006.01) | |
| *C07C 7/12* | (2006.01) | |

(52) U.S. Cl.
CPC ....... *B01J 20/0244* (2013.01); *B01J 20/0277* (2013.01); *B01J 20/043* (2013.01); *B01J 20/06* (2013.01); *B01J 20/28011* (2013.01); *B01J 20/28057* (2013.01); *B01J 20/28071* (2013.01); *B01J 20/3078* (2013.01); *C01G 9/00* (2013.01); *C01G 9/04* (2013.01); *C07C 7/12* (2013.01); *B01D 2253/104* (2013.01); *B01D 2253/112* (2013.01); *B01D 2253/25* (2013.01); *B01D 2257/2045* (2013.01); *C01P 2002/72* (2013.01)

(58) Field of Classification Search
CPC ................ B01J 20/28011; B01J 20/043; B01J 20/0244; B01J 20/06; C01G 9/04; C01G 9/00; B01D 53/685; B01D 53/02; B01D 53/04; B01D 2253/25; B01D 2253/104; B01D 2257/2045; B01D 2253/112; C07C 7/12; C01P 2002/72
See application file for complete search history.

(56) References Cited

U.S. PATENT DOCUMENTS

| | | |
|---|---|---|
| 3,935,295 A | 1/1976 | La Hue et al. |
| 3,943,226 A | 3/1976 | Difford |
| 4,639,259 A | 1/1987 | Pearson |
| 5,505,926 A | 4/1996 | Lee et al. |
| 5,935,894 A | 8/1999 | Kanazirev |
| 6,558,641 B1* | 5/2003 | Bailey .................... B01D 53/68 |
| | | 423/240 R |
| 7,064,097 B1 | 6/2006 | Cai et al. |
| 7,758,837 B2 | 7/2010 | Kanazirev |
| 7,790,130 B2 | 9/2010 | Kanazirev |
| 7,947,621 B2 | 5/2011 | Chang et al. |
| 8,551,328 B2 | 10/2013 | Maglio et al. |
| 2011/0142946 A1* | 6/2011 | Tabata .................... A61K 9/143 |
| | | 424/489 |
| 2014/0296607 A1 | 10/2014 | Baptist et al. |
| 2016/0166970 A1* | 6/2016 | Boehringer ............ B01D 53/02 |
| | | 423/210 |
| 2016/0279596 A1* | 9/2016 | Evans ...................... B01J 20/08 |

FOREIGN PATENT DOCUMENTS

| | | |
|---|---|---|
| CN | 102463098 A | 5/2012 |
| EP | 0933127 A1 | 8/1999 |
| RU | 2211085 C1 | 8/2003 |
| WO | 9939819 | 8/1999 |
| WO | 2005047438 A1 | 5/2005 |
| WO | 2007030677 A2 | 3/2007 |
| WO | 2013045883 A1 | 4/2013 |

OTHER PUBLICATIONS

Nobuyoshi Koga, et al., Kinetic approach to partially overlapped thermal decomposition processes, Co-precipitated zinc carbonates, J. Thermal Anal. Calorim (2013) 111:1463-1474.

Extended European Search Report for corresponding European application No. 16835809.1, dated Mar. 20, 2019.

Howard, "Progress toward biomass and coal-derived syngas warm cleanup: Proof-of-concept process demonstration of multicontaminant removal for biomass application" Industrial and Engineering Chemistry Research (2013), v 52, n. 24, p. 8125-8138.

Search Report dated Nov. 10, 2016 for corresponding PCT Appl. No. PCT/US2016/046270.

Written Opinion from PCT application No. PCT/US2016/046270, dated Oct. 31, 2016.

\* cited by examiner

COMPOSITION AND PROCESS FOR REMOVING CHLORIDES FROM A GASEOUS STREAM

CROSS-REFERENCE TO RELATED APPLICATIONS

This application is a Continuation of International Application No. PCT/US2016/046270 filed Aug. 10, 2016 which application claims benefit of U.S. Provisional Application No. 62/204,108 filed Aug. 12, 2015, the contents of which cited applications are hereby incorporated by reference in their entirety.

FIELD OF THE INVENTION

The present invention relates to a method for treating hydrocarbon streams to remove acid gases. More particularly, the present invention relates to a process using a catalytically inert sorbent for removing HCl from hydrocarbon-containing streams.

BACKGROUND OF THE INVENTION

Petroleum refining and petrochemical processes frequently involve acid gases which are present as impurities in numerous industrial fluids, i.e., liquid and gas streams. These acid gases include hydrogen halides such as HCl, HF, HBr, HI and mixtures thereof.

For example, one of the key processes in refining petroleum is catalytic reforming. In the catalytic reforming process, a light petroleum distillate or naphtha range material is passed over a noble metal catalyst to produce a high octane product. Hydrogen is a by-product of the catalytic reforming process, and a portion of the byproduct hydrogen is recycled to the reaction zone to maintain catalyst stability. Typically, the noble metal reforming catalyst is promoted with chloride which, in the presence of hydrogen, results in the production of a small amount of hydrogen chloride. Thus, the net byproduct hydrogen withdrawn from the catalytic reforming process generally contains a small amount of hydrogen chloride.

Similarly, in a process for the dehydrogenation of light iso-paraffins to produce iso-olefins, the promoting of the noble metal catalyst with chloride will produce a net hydrogen stream containing small amounts of HCl. The net hydrogen produced in the catalytic reforming process and the dehydrogenation process is generally used in sensitive downstream catalytic processes. In addition, there are other hydrocarbon and chemical processes in which small amounts of HCl are generated and carried away in gas or liquid streams.

Even small amounts of gaseous HCl present in the net hydrogen can seriously interfere with the operation of downstream processes which use the hydrogen and can cause corrosion problems in the equipment such as pipes, valves, and compressors which convey hydrogen. Generally, HCl in gas or liquid hydrocarbon streams must be removed from such streams to prevent unwanted catalytic reactions and corrosion of process equipment. Furthermore, HCl is considered a hazardous material and releasing the HCl to the environment must be avoided.

Existing sorption processes for removing HCl from hydrocarbon-containing streams typically involve passing the hydrocarbon-containing fluid stream over a sorbent, which is disposed in a fixed bed. There are various formulations that are currently used as sorbents to remove chlorides from various streams.

For example, some sorbents comprise alumina. However, the alumina sorbents generally have a low capacity and the spent material had a high reactivity (of HCl on the surface) tending to form "green oil." Typically, these green oils are green or red in color and generally contain chlorinated $C_6$ to $C_{18}$ hydrocarbons and are believed to be oligomers of light olefinic hydrocarbons. The presence of green oils in the fixed sorbent bed fouls the sorbent bed and results in the premature failure of the sorbent. When this fouling occurs, often costly measures are required to remove the spent sorbent from the bed. Furthermore, the chloride content of the green oils on the spent sorbent makes disposal of the spent sorbent an environmental problem. While the exact mechanism of green oil formation is unknown, it is believed that green oils are formed by catalytic reaction of aluminum chloride or HCl with the hydrocarbon. Green oil formation remains an unresolved industry problem during the removal of HCl from hydrocarbon streams.

Some alumina sorbents have been doped with various additives, such as alkali or alkaline earth elements, to improve the performance of the chloride scavengers. See, U.S. Pat. Nos. 3,557,025; 3,943,226; 4,639,259; 5,505,926; and 5,935,894.

Furthermore, some chloride sorbents comprise a zeolite which acts as a molecular sieve to trap the chloride compounds within the pores of the zeolite. See, U.S. Pat. No. 8,551,328. However, the chloride capacity per gram is lower, making the use of same impracticable.

Finally, some chloride sorbents utilize metal oxide with a binder such as alumina or others which, like the activated alumina sorbents, remove chloride compounds via an acid-base reaction. While presumably effective for their intended uses, it is believed that such sorbents have a lower capacity due to the use of a binder which takes away from the amount of active material that may be in such compositions.

The appropriate chloride sorbent may depend on the particular applications of type of use. For example, catalytic reforming processes can often include continuous catalyst regeneration which produces gas streams that are non-fouling, dry, and can be subjected to long contact times with a sorbent. It is believed that chloride adsorbents with high capacities would be useful in such applications.

It is desirable to discover new sorbents which can be used in such processes. It is further desirable to discover and develop sorbents with different properties, such as activity and selectivity.

SUMMARY OF THE INVENTION

One or more new compositions for removing chloride compounds from a stream and processes for using same have been invented. The compositions do not include a significant portion of binder, making the capacity of the adsorbent relatively high. Furthermore, the crush strength and affinity to produce green oil compared to conventional adsorbents, makes the compositions of the sorbents desirable for various chloride scavenging processes.

In a first aspect of the present invention, the present invention may broadly be characterized as providing a composition comprising, at least, a first zinc carbonate, a second zinc carbonate different than the first zinc carbonate, and an alumina material. The alumina material comprises less than 10 wt % of the composition. The first zinc carbonate comprises hydrozincite. Additionally, the composition has been cured (i.e., calcined) at a temperature between about 149 to 399° C. (about 300 to 750° F.).

In various embodiments of the present invention, the second zinc carbonate comprises smithsonite.

In at least one embodiment of the present invention, the alumina comprises less than 5 wt % of the composition.

In many embodiments of the present invention, the composition includes at least two pairs of x-ray diffraction peaks at a two-theta value selected from a group consisting of: about 12.80 and about 17.30; about 13.00 and about 36.00; and, about 25.00 and about 32.50. It is further contemplated that the composition further includes at least one x-ray diffraction peak or pair of peaks at a two-theta value selected from a group consisting of: about 34.30; about 35.00 and 38.00; and, about 30.50 and about 34.50.

In some embodiments of the present invention, the composition has been cured at a temperature between about 260 to 316° C. (500 to 600° F.).

In many embodiments of the present invention, the composition lacks an x-ray diffraction peak at a two-theta value of about 14.50.

In various embodiments of the present invention, the composition further comprises zinc oxide.

In one or more embodiments of the present invention, the composition comprises about 42 wt % zinc. It is further contemplated that the composition further comprises about 16 wt % sodium.

In a second aspect of the present invention, the present invention may generally be characterized as providing a composition for adsorbing chloride compounds, the composition comprising, at least, a first zinc carbonate comprising hydrozincite or smithsonite, a second zinc carbonate different than the first zinc carbonate, an alumina material, and, zinc oxide.

In one or more embodiments of the present invention, the composition includes at least two pairs of x-ray diffraction peaks at a two-theta value selected from a group consisting of: about 12.80 and about 17.30; about 13.00 and about 36.00; and, about 25.00 and about 32.50.

In various embodiments of the present invention, the first zinc carbonate comprises hydrozincite, and wherein the second zinc carbonate comprises smithsonite. It is contemplated that the composition has been cured at a temperature between 260 to 316° C. (500 to 600° F.).

In many embodiments of the present invention, the composition further comprises sodium carbonate. It is contemplated that the composition comprises about 42 wt % zinc and about 16 wt % sodium.

In some embodiments of the present invention, the composition is substantially free of boehmite.

In yet a third aspect of the present invention, the present invention may generally be characterized as providing a process for removing chloride compounds from a gaseous stream by: passing a gaseous stream to an adsorption zone, the adsorption zone comprising an adsorbent and being operated under conditions to remove chloride compounds from the gaseous stream, wherein the adsorbent comprises a first zinc carbonate being hydrozincite or smithsonite, a second zinc carbonate different than the first zinc carbonate, and, zinc oxide.

In one or more embodiments of the present invention, the adsorbent comprises about 42 wt % zinc. It is contemplated that the first zinc carbonate comprises smithsonite, and the second zinc carbonate comprises hydrozincite. It is further contemplated that the adsorbent is substantially free of boehmite.

Additional aspects, embodiments, and details of the invention, all of which may be combinable in any manner, are set forth in the following detailed description of the invention.

BRIEF DESCRIPTION OF THE DRAWINGS

One or more exemplary embodiments of the present invention will be described below in conjunction with the following drawing figures, in which.

DETAILED DESCRIPTION OF THE INVENTION

Figure 1:
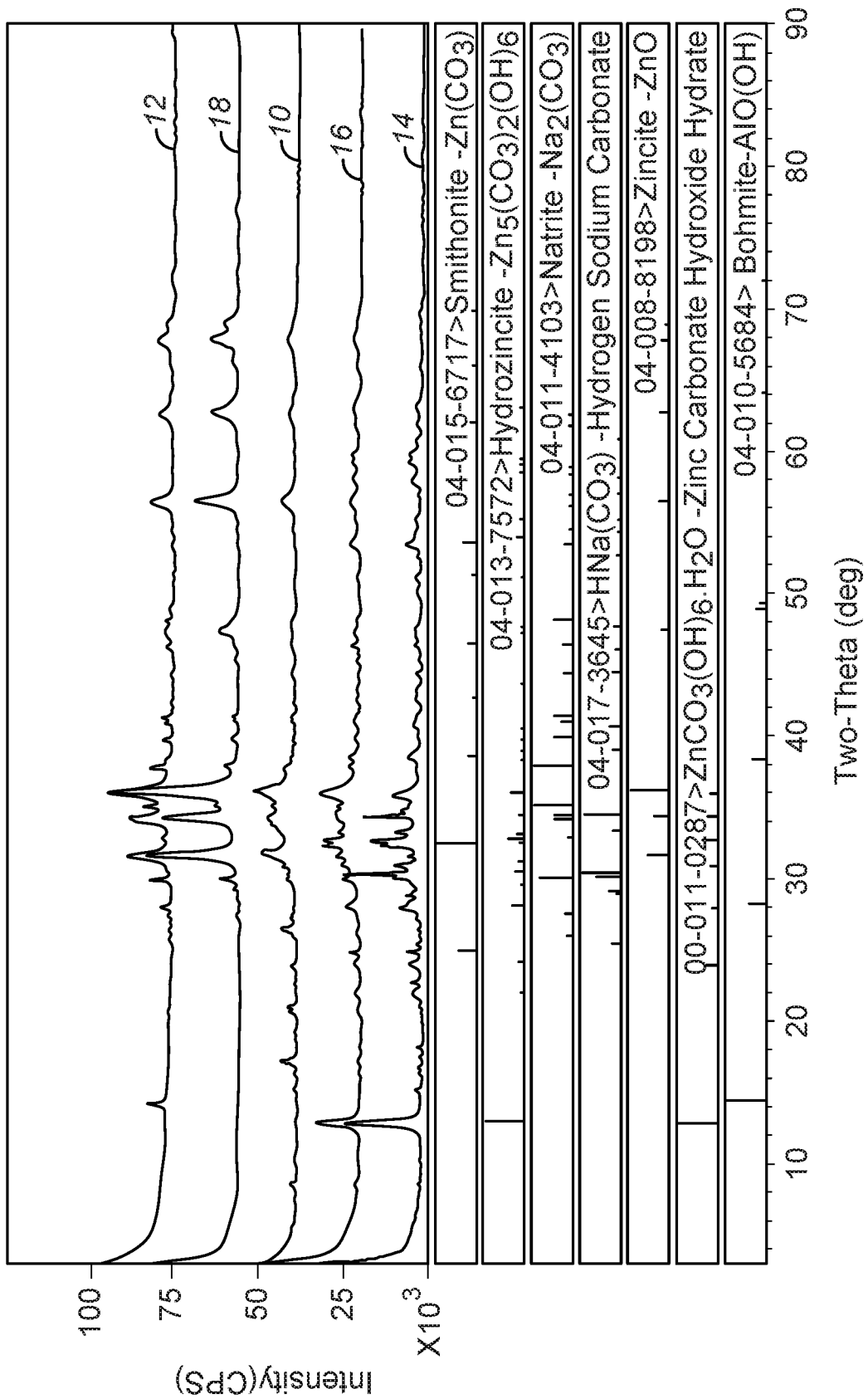
FIG. 1 shows a comparison of an x-ray diffraction of various samples according to the present invention, as well as two commercially available products; and, FIG. 2 shows a comparison of the cumulative intrusion compared to the pore size for various samples according to the present invention, and one commercially available product.

The invention is described in preferred embodiments in the following description. Reference throughout this specification to "one embodiment," "an embodiment," or similar language means that a particular feature, structure, or characteristic described in connection with the embodiment is included in at least one embodiment of the present invention. Thus, appearances of the phrases "in one embodiment," "in an embodiment," and similar language throughout this specification may, but do not necessarily, all refer to the same embodiment.

The terms sorbent, adsorbent, and absorbent as used herein refer to the ability of a material to take in or soak up liquid or gas components on the surface thereof or to assimilate such components into the body thereof.

As mentioned above, a composition capable of removing chlorides from a gaseous stream and a process of using same have been invented. The compositions have sufficient chloride capacity, offer comparable creation of green oil, and have sufficient structural integrity to be utilized as sorbents in a chloride removal process.

With these general principles in mind, one or more embodiments of the present invention will be described with the understanding that the following description is not intended to be limiting.

In a broad aspect, the compositions of the present invention comprise at least two zinc carbonates and an alumina material, such aluminum oxide ($Al_2O_3$). The two zinc carbonates are different from each other. At least one of zinc carbonates is hydrozincite ($Zn_5(CO_3)_2(OH)_6$) or smithsonite (zinc carbonate ($ZnCO_3$)). It is preferred that one of the zinc carbonates is hydrozincite and the other zinc carbonate is smithsonite.

The alumina used in the compositions of the present invention preferably comprises less than about 10% by weight (wt %) of the composition, or less than about 5 wt % of the composition. Throughout this application, the term "about" with respect to weight percentages means +/−5, or +/−2.5, or +/−1. While the compositions of the present invention include alumina, the compositions are essentially free of boehmite (aluminum oxide hydroxide (AlO(OH)).

In addition to the two zinc carbonates and the alumina, the compositions may include other materials, including, for example zinc oxide (ZnO), natrite ($Na_2CO_3$), nahcolite ($NaHCO_3$), and zinc oxalate hydroxide ($Zn_2C_2O_4.3Zn(OH)_2$). The compositions may comprise about 42 wt % zinc and about 16 wt % sodium, and between 0 to 10 wt % aluminum. These weight percentages reflect the metal salts, such as an oxide, carbonate, bicarbonate, hydroxide, hydrocarbonate, etc. In the compositions, a molar ratio of sodium to zinc may be between about 0.95 to 1.10. Additionally, in the compositions, a molar ratio of sodium to alumina may be between about 5.0 to 6.0.

At least two solid and one liquid component are needed to produce the reactive composite composition of the present invention which can be formed into materials to be used as a sorbent. A first solid preferably comprises an alkali metal carbonate in a powder form. Small particles, preferably about 5 to 10 microns in diameter, are employed. One carbonate component that has been found to provide excellent results in the present invention is the natural carbonate (soda ash) ore known as Trona, however, other solids that can be used include Nahcolite, Wegscheiderite ($Na_2CO_3.NaHCO_3$), Thermonatrite ($Na_2CO_3.H_2O$), Shortite ($Na_2CO_3.2CaCO_3$), and Eitelite ($Na_2CO_3.MgCO_3$). One such carbonate that has been found especially useful is a natural sodium sesquicarbonate, marketed by Solvay Chemicals, Houston, Tex. as Solvay T-200®. A sesquicarbonate has a formula of $Na_2CO_3.NaHCO_3.2H_2O$. It produces 1.5 mols sodium carbonate ($Na_2CO_3$) upon heating at sufficiently high temperature. Other solids that can be used include Nahcolite, Wegscheiderite ($Na_2CO_3.NaHCO_3$), Thermonatrite ($Na_2CO_3.H_2O$), Shortite ($Na_2CO_3.2CaCO_3$), and Eitelite ($Na_2CO_3.MgCO_3$).

The second solid material zinc carbonate preferably comprises of following characteristics in Table 1, below.

TABLE 1

| Determination | Units | Specification Min | Specification Max |
|---|---|---|---|
| Zinc As Zn | % | 56 | 60 |
| Lead As Pb (dried basis) | % | 0 | 0.1 |
| Other heavy metals (dried basis) | % | 0 | 0.3 |
| Sulphur as S (Room Temp) | % | 0 | 0.3 |
| Sodium Oxide as $Na_2O$ (Room Temp) | % | 0 | 1 |
| Surface Area | $m^2/g$ | 50 | |
| LOD at 1050° C. | % | 0 | 2 |
| Tapped Bulk Density (tapped to constant volume) | Lbs./$ft^3$ | 25 | 50 |
| Chloride as Cl | ppm | 0 | 1000 |

The third component is water, or optionally an aqueous solution of a salt, which plays an important role in facilitating a reaction between the carbonate and alumina powder. The preferred metal salt is selected from the group consisting of sodium carbonate and sodium silicate.

Additional components may be added to enhance porosity or strength.

After the components are mixed, for example in a nodulizer, the produced particles are cured (or calcined) at a temperature between 149 to 399° C. (about 300 to 750° F.), or between about 260 to 316° C. (500 to 600° F.) for approximately 1 hour, however, other times may be utilized. During the heating, hydrozincite is formed. Additionally, smithsonite and hydrozincite will decompose to varying extents to form zinc oxide. Furthermore, as a result of the curing, the Trona converts to sodium carbonate. The resulting cured particles will include at least one, and preferably both, of smithsonite and hydrozincite.

A sample new sorbent was made by using the Nodulization technique disclosed in U.S. Pat. No. 7,758,837. A powder blend by using T-200® sesquicarbonate and basic $ZnCO_3$ at a molar ratio of sodium to zinc of about 0.95-1.10 was placed in a small rotating pan made from the bottom of a plastic bottle. The pan had a diameter of about 12.7 cm (5 inches) and a height of about 15.2 cm (6 inches). It was rotated at about 120 rpm at an inclination of about 45 degrees. The powder blend was occasionally stirred using a spatula and hand sprayed with water to form particulates. A total of about 20 g water was added before the particulates began to stick together. At that point, the addition of water was ceased and a small amount of additional blend was added in order to restore the free flowing pattern of the particulates. The particulates had a broad particle size distribution ranging from about 40 mesh to about 3 mesh. Other than some spherical beads, most of the particles had a rather irregular form. All particulates were placed in a closed glass container and allowed to settled for about 2 hours followed by curing at 149° C. (300° F.), 260° C. (500° F.), and 399° C. (750° F.), respectively for about 1 hour in an air circulated oven. The material lost about 30% of its weight upon curing. After cooling, the size fraction 5×8 mesh of the particulates was screened out for further testing, XRD and Cl pickup in particular.

FIG. 1 depicts an x-ray diffraction of the three samples. Additionally, two different samples of a commercially available sorbent are also depicted on FIG. 1—one having essentially no zinc (#1) and one including an alumina binder (#2). The compositions of the three new samples and two commercially available products are depicted in TABLE 2, below.

TABLE 2

| Samples (ref. no. in FIG. 1) | Zn wt % | Na wt % | Al wt % | Mol Na/Zn | Mol Na/Al | Crush Strength |
|---|---|---|---|---|---|---|
| Commercially available #1 (10) | 0 | 9.33 | 40.4 | — | 0.27 | 6.0 Lbf |
| Commercially available #2 (12) | 25.6 | 13.8 | 12.3 | 1.53 | 1.31 | 2.5 Lbf |
| New cured at 149° C. (14) | 40-44 | 15-17 | 0-10 | .95-1.10 | 5-6 | 8 Lbf |
| New cured at 260° C. (16) | 40-44 | 15-17 | 0-10 | .95-1.10 | 5-6 | 6.5 Lbf |
| New cured at 399° C. (18) | 40-44 | 15-17 | 0-10 | .95-1.10 | 5-6 | 3 Lbf |

As shown in FIG. 1, the x-ray diffraction of the new sample 14 cured at 149° C. indicated the presence of hydrozincite and smithsonite along with zincite (ZnO), natrite ($Na_2(CO_3)$), nacolite ($NaHCO_3$), zinc oxalate hydroxide ($Zn_2C_2O_4.3Zn(OH)_2$). Additionally, the x-ray diffraction of the new sample 16 cured at 260° C. indicated the presence of hydrozincite and smithsonite along with zincite (ZnO), natrite ($Na_2(CO_3)$), nacolite ($NaHCO_3$), zinc oxalate hydroxide ($Zn_2C_2O_4.3Zn(OH)_2$).

In contrast, an x-ray diffraction of the new sample 18 cured at 399° C. (750° F.) indicated the presence of zincite, and natrite, but no hydrozincite or smithsonite. A similar x-ray diffraction of the commercially available sample 12 which includes an alumina binder indicated the presence of zincite, natrite and boehmite, but no hydrozincite or smithsonite. Finally, the x-ray diffraction of the commercially available sample 10 that was relatively free of zinc indicated no zinc compounds in the sample.

Thus, in general an x-ray diffraction of a composition according to the present invention, would have at least one set of two-theta peaks at: 25.00 and 32.50 (indicating smithsonite); 13.00 and 36.00 (indicating hydrozincite); or, 12.80 and 17.30 (unidentified, but possibly zinc carbonate hydroxide hydrate). In some embodiments, the compositions would have two of these three sets of peaks, or all three sets. The compositions may also include additional materials, and, for example, an x-ray diffraction may include two-theta peaks at: 34.30 (indicating zincite); 35.00 and 38.00 (indicating natrite); and, 30.50 and 34.50 (indicating hydrogen sodium carbonate). Furthermore, in the composition according to the present invention, an x-ray diffraction should indicate the lack of a two-theta peak at 14.50 (for boehmite).

Figure 2:
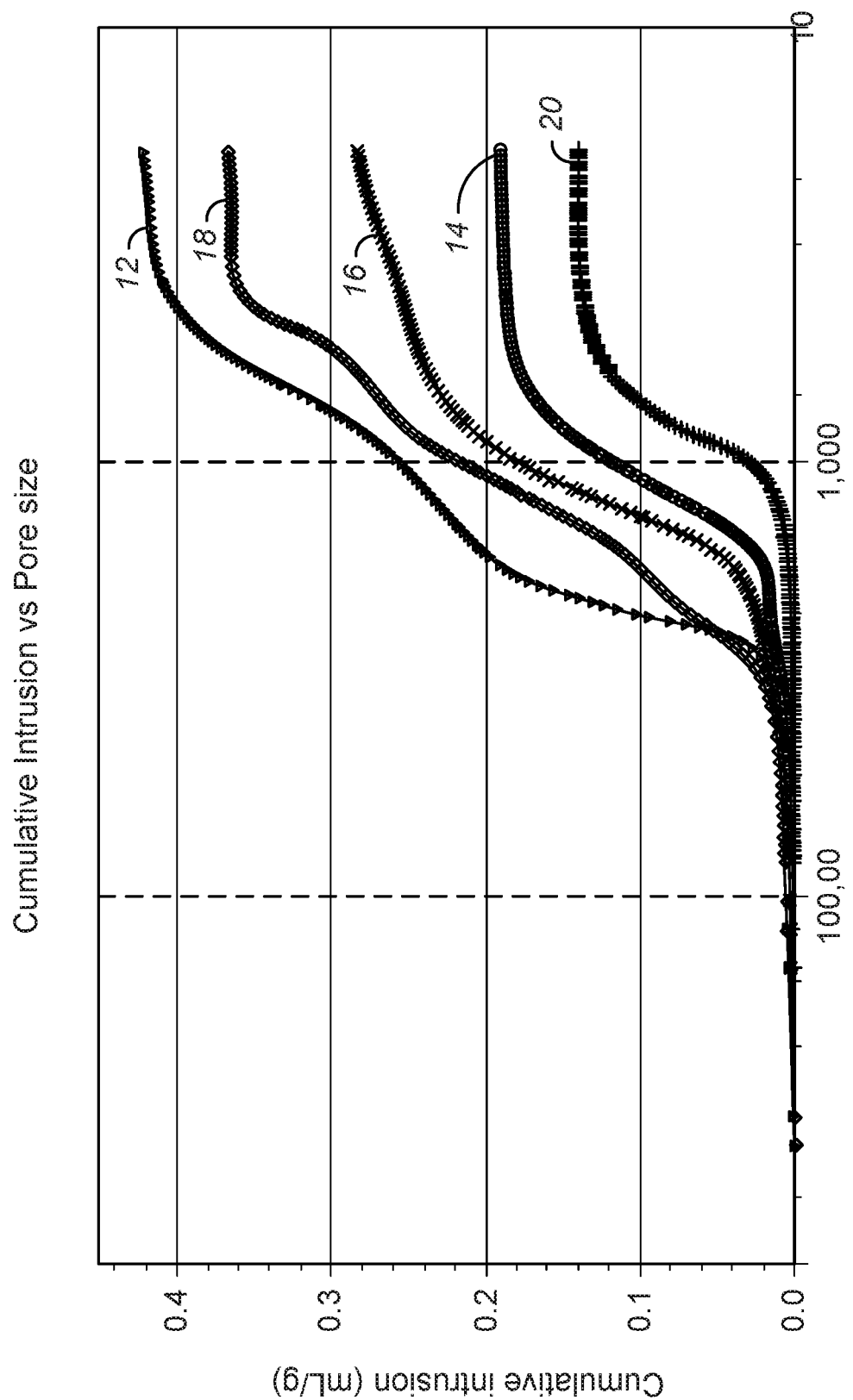

FIG. 2 shows the cumulative intrusion compared to the pore diameter for the three samples discussed above, along with an uncured sample of the new sorbent 20, as well as commercially available sample 12 which includes an alumina binder, discussed above with respect to FIG. 1. As should be appreciated, FIG. 2 indicates that the commercially available sample 12 which includes an alumina binder has the greatest, total pore volume. While this may be generally desirable, as shown above in TABLE 2, the commercially available sample 12 which includes an alumina binder has the lowest crush strength. Furthermore, as demonstrated in FIG. 2, the relationship between the cure temperature of the new sorbents and the total pore volume of the samples, as well as the crush strength from TABLE 2, is not a linear relationship.

A comparison of the theoretical chloride capacity of the new sample compared to the two commercially available samples discussed above in FIG. 1 is shown below in TABLE 3.

TABLE 3

| | Bed Density (g/cc) | BET SA ($m^2/g$) | Pore Volume (cc/g) | Theoretical Chloride Capacity (g Cl/100 g sample) |
|---|---|---|---|---|
| Commercially available #1 (10) | 0.827 | 170 | 0.289 | 14.4 |
| Commercially available #2 (12) | 0.751 | 73 | 0.170 | 49.0 |
| New sample | 0.85-.95 | 30-35 | 0.130 | 69.5 |

Accordingly, based upon the data in TABLE 3, the new sample had smaller pore volume, but greater theoretical chloride capacity. In testing, samples prepared according to the present invention showed a 48% longer cycle length for a 10 second contact time compared to the commercially available sample 12 which includes an alumina binder. For a 15 second contact time experiment, the sample prepared according to the present invention has a 33% longer cycle length compared to the commercially available sample 12 which includes an alumina binder.

It is believed that the improved qualities and characteristics of the present invention may be due to the increased amount of active material, and less binder. Although not intending to be bound by any particular theory, it is believed that the zinc in the compounds of the present invention are more dispersed with a greater formation of $Na_2ZnCl_4$.

Thus, the compounds according to the present invention, are believed to at least achieve the same chloride capacity as existing compounds, with a greater crush strength and with about the same propensity to produce green oil as existing compounds. Thus, the compositions could be used to remove chloride compounds from gas streams, in particular, gas streams associated with petrochemical processes, especially those in which chloride compounds are likely to form, such as the off gas stream of a catalytic reforming unit.

It should be appreciated and understood by those of ordinary skill in the art that specifics of same aspects of the present invention are well within the knowledge of those of ordinary skill in the art and a description of same is not necessary for practicing or understanding the embodiments of the present invention.

Indeed, the use of such an adsorbent is well within the skill of those of ordinary skill in the art. For example, the adsorbent could be loaded into a vessel. Any particular vessel could be used, and the vessel may include multiple beds. A stream including a chloride contaminant could be introduced into the vessel, and a purified stream having a lower concentration of chlorides may be recovered. More than one vessel may be provided, for example, in a lead-lag configuration. One of ordinary skill in the art will appreciate that the foregoing brief description may have excluded equipment which is typically used such as valves, pumps, filters, coolers, etc. as it is believed that the specifics of same are well within the knowledge of those of ordinary skill in the art and a description of same is not necessary for practicing or understanding the embodiments of the present invention.

SPECIFIC EMBODIMENTS

While the following is described in conjunction with specific embodiments, it will be understood that this description is intended to illustrate and not limit the scope of the preceding description and the appended claims.

A first embodiment of the invention is a composition comprising a first zinc carbonate; a second zinc carbonate different than the first zinc carbonate; an alumina material, wherein the alumina comprises less than 10 wt % of the composition, and wherein the first zinc carbonate comprises hydrozincite, and wherein the composition has been cured at a temperature between 149 to 399° C. An embodiment of the invention is one, any or all of prior embodiments in this paragraph up through the first embodiment in this paragraph wherein the second zinc carbonate comprises smithsonite. An embodiment of the invention is one, any or all of prior embodiments in this paragraph up through the first embodiment in this paragraph wherein the alumina comprises less than 5 wt % of the composition. An embodiment of the invention is one, any or all of prior embodiments in this paragraph up through the first embodiment in this paragraph wherein the composition includes at least two pairs of x-ray diffraction peaks at a two-theta value selected from the group consisting of about 12.80 and about 17.30; about 13.00 and about 36.00; and, about 25.00 and about 32.50. An embodiment of the invention is one, any or all of prior embodiments in this paragraph up through the first embodiment in this paragraph, wherein the composition further includes at least one x-ray diffraction peak or pair of peaks at a two-theta value selected from the group consisting of about 34.30; about 35.00 and 38.00; and, about 30.50 and about 34.50. An embodiment of the invention is one, any or all of prior embodiments in this paragraph up through the first embodiment in this paragraph wherein the composition has been cured at a temperature between 260 to 316° C. An embodiment of the invention is one, any or all of prior embodiments in this paragraph up through the first embodiment in this paragraph wherein the composition lacks an x-ray diffraction peak at a two-theta value of about 14.50. An embodiment of the invention is one, any or all of prior embodiments in this paragraph up through the first embodiment in this paragraph further comprising zinc oxide. An embodiment of the invention is one, any or all of prior embodiments in this paragraph up through the first embodiment in this paragraph further comprising about 42 wt % zinc. An embodiment of the invention is one, any or all of prior embodiments in this paragraph up through the first embodiment in this paragraph further comprising about 16 wt % sodium.

A second embodiment of the invention is a composition for adsorbing chloride compounds, the composition comprising a first zinc carbonate, wherein the first zinc carbonate comprises hydrozincite or smithsonite; a second zinc carbonate different than the first zinc carbonate; an alumina material; and, zinc oxide. An embodiment of the invention is one, any or all of prior embodiments in this paragraph up through the second embodiment in this paragraph wherein the composition includes at least two pairs of x-ray diffraction peaks at a two-theta value selected from the group consisting of about 12.80 and about 17.30; about 13.00 and about 36.00; and, about 25.00 and about 32.50. An embodiment of the invention is one, any or all of prior embodiments in this paragraph up through the second embodiment in this paragraph wherein the first zinc carbonate comprises hydrozincite, and wherein the second zinc carbonate comprises smithsonite. An embodiment of the invention is one, any or all of prior embodiments in this paragraph up through the second embodiment in this paragraph, wherein the composition has been cured at a temperature between 260 to 316° C. An embodiment of the invention is one, any or all of prior embodiments in this paragraph up through the second embodiment in this paragraph further comprising sodium carbonate. An embodiment of the invention is one, any or all of prior embodiments in this paragraph up through the second embodiment in this paragraph wherein the composition comprises about 42 wt % zinc and about 16 wt % sodium. An embodiment of the invention is one, any or all of prior embodiments in this paragraph up through the second embodiment in this paragraph wherein the composition is substantially free of boehmite.

A third embodiment of the invention is a process for removing chloride compounds from a gaseous stream, the process comprising passing a gaseous stream to an adsorption zone, the adsorption zone comprising an adsorbent and being operated under conditions to remove chloride compounds from the gaseous stream, wherein the adsorbent comprises a first zinc carbonate being hydrozincite or smithsonite, a second zinc carbonate different than the first zinc carbonate, and, zinc oxide. An embodiment of the invention is one, any or all of prior embodiments in this paragraph up through the third embodiment in this paragraph wherein the adsorbent comprises about 42 wt % zinc. An embodiment of the invention is one, any or all of prior embodiments in this paragraph up through the third embodiment in this paragraph wherein the first zinc carbonate comprises smithsonite, and wherein the second zinc carbonate comprises hydrozincite, and wherein the adsorbent is substantially free of boehmite.

Without further elaboration, it is believed that using the preceding description that one skilled in the art can utilize the present invention to its fullest extent and easily ascertain the essential characteristics of this invention, without departing from the spirit and scope thereof, to make various changes and modifications of the invention and to adapt it to various usages and conditions. The preceding preferred specific embodiments are, therefore, to be construed as merely illustrative, and not limiting the remainder of the disclosure in any way whatsoever, and that it is intended to cover various modifications and equivalent arrangements included within the scope of the appended claims.

In the foregoing, all temperatures are set forth in degrees Celsius and, all parts and percentages are by weight, unless otherwise indicated.

While at least one exemplary embodiment has been presented in the foregoing detailed description of the invention, it should be appreciated that a vast number of variations exist. It should also be appreciated that the exemplary embodiment or exemplary embodiments are only examples, and are not intended to limit the scope, applicability, or configuration of the invention in any way. Rather, the foregoing detailed description will provide those skilled in the art with a convenient road map for implementing an exemplary embodiment of the invention, it being understood that various changes may be made in the function and arrangement of elements described in an exemplary embodiment without departing from the scope of the invention as set forth in the appended claims and their legal equivalents.

What is claimed is:

1. A composition comprising:
   a first zinc carbonate;
   a second zinc carbonate different than the first zinc carbonate;
   sodium carbonate;
   an alumina material, wherein the alumina material comprises less than 10 wt % of the composition, and
   wherein the first zinc carbonate comprises hydrozincite,
   wherein a molar ratio of sodium to zinc is between 0.95 to 1.10,
   wherein a molar ratio of sodium to alumina is at least 5, and
   wherein the composition has been cured at a temperature between 149 to 316° C.

2. The composition of claim 1 wherein the second zinc carbonate comprises smithsonite.

3. The composition of claim 1 wherein the alumina material comprises less than 5 wt % of the composition.

4. The composition of claim 1 wherein the composition includes at least two pairs of x-ray diffraction peaks at a two-theta value selected from a group consisting of: about 12.80 and about 17.30; about 13.00 and about 36.00; and, about 25.00 and about 32.50.

5. The composition of claim 4, wherein the composition further includes at least one x-ray diffraction peak or pair of peaks at a two-theta value selected from a group consisting of: about 34.30; about 35.00 and 38.00; and, about 30.50 and about 34.50.

6. The composition of claim 1 wherein the composition lacks an x-ray diffraction peak at a two-theta value of about 14.50.

7. The composition of claim 1 further comprising: zinc oxide.

8. The composition of claim 7 further comprising: about 16 wt % sodium.

9. The composition of claim 1 further comprising: about 42 wt % zinc.

10. The composition of claim 1, wherein the molar ratio of sodium to alumina is between 5 to 6.

11. A composition for adsorbing chloride compounds, the composition comprising:
    a first zinc carbonate, wherein the first zinc carbonate comprises hydrozincite or smithsonite;
    a second zinc carbonate different than the first zinc carbonate;
    sodium carbonate;
    an alumina material; and,
    zinc oxide, and
    wherein a molar ratio of sodium to alumina is between 5.0 to 6.0,
    wherein a molar ratio of sodium to zinc is between 0.95 to 1.10, wherein the composition has been cured at a temperature between 149 to 316° C., and wherein the alumina material comprises less than 10 wt % of the composition.

12. The composition of claim 11 wherein the composition includes at least two pairs of x-ray diffraction peaks at a two-theta value selected from a group consisting of: about 12.80 and about 17.30; about 13.00 and about 36.00; and, about 25.00 and about 32.50.

13. The composition of claim 11 wherein the first zinc carbonate comprises hydrozincite, and wherein the second zinc carbonate comprises smithsonite.

14. The composition of claim 13, wherein the composition has been cured at a temperature between 260 to 316° C.

15. The composition of claim 11 wherein the composition comprises about 42 wt % zinc and about 16 wt % sodium.

16. The composition of claim 11 wherein the composition is substantially free of boehmite.

17. A process for removing chloride compounds from a gaseous stream, the process comprising:

passing a gaseous stream to an adsorption zone, the adsorption zone comprising an adsorbent and being operated under conditions to remove chloride compounds from the gaseous stream, wherein the adsorbent comprises a first zinc carbonate being hydrozincite or smithsonite, a second zinc carbonate different than the first zinc carbonate, sodium carbonate, an alumina material, wherein the alumina material comprises less than 10 wt % of the adsorbent and, zinc oxide, wherein a molar ratio of sodium to alumina is at least 5.0, wherein a molar ratio of sodium to zinc is between 0.95 to 1.10, and wherein the composition has been cured at a temperature between 149 to 316° C.

18. The process of claim 17 wherein the adsorbent comprises about 42 wt % zinc.

19. The process of claim 18 wherein the first zinc carbonate comprises smithsonite, and wherein the second zinc carbonate comprises hydrozincite, and wherein the adsorbent is substantially free of boehmite.

* * * * *